United States Patent [19]

Miyasaka et al.

[11] Patent Number: 6,080,737
[45] Date of Patent: Jun. 27, 2000

[54] UVEITIS REMEDY

[75] Inventors: Nobuyuki Miyasaka; Miki Hiraoka, both of Tokyo, Japan

[73] Assignee: Chugai Seiyaku Kabushiki Kaisha, Tokyo, Japan

[21] Appl. No.: 09/142,541

[22] PCT Filed: Mar. 18, 1997

[86] PCT No.: PCT/JP97/00854

§ 371 Date: Sep. 10, 1998

§ 102(e) Date: Sep. 10, 1998

[87] PCT Pub. No.: WO97/34606

PCT Pub. Date: Sep. 25, 1997

[30] Foreign Application Priority Data

Mar. 19, 1996 [JP] Japan ........................ 8-62740

[51] Int. Cl.[7] .................... A61K 31/54; A61K 31/505
[52] U.S. Cl. ........................... 514/224.2; 514/258
[58] Field of Search ................... 514/224.2, 258

[56] References Cited

U.S. PATENT DOCUMENTS 5,354,753  10/1994  Ohi et al. .................... 514/258
5,728,692  3/1998  Ohi et al. .................... 514/224.2

OTHER PUBLICATIONS

McMaster et al., "Prevention of Experimental Allergic Uveitis", *Arch Ophthamol*, 93:835–837, (1975).

Lazar et al., "Treatment of Uveitis with Methotrexate", *American Journal of Opthalmology*, vol. 67, no. 3, 383–387, (1969).

Wong, "Immunosuppressive Therapy of Ocular Inflammatory Disease", *Arch Ophthalmol*, 81:628–637, (1969).

Hemady, "Immunosuppressive Drugs in Immune and Inflammatory Ocular Disease", *Survey of Ophthalmology*, vol. 35, No. 5, 369–385, (1991).

*Primary Examiner*—Raymond Henley, III
*Attorney, Agent, or Firm*—Browdy and Neimark

[57] ABSTRACT

Remedies for uveitis which contain, as the active ingredient, one or more compounds represented by the following general formula (I) or salts thereof:

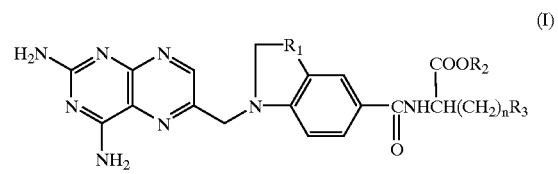

wherein $R_1$ represents a member selected from the group consisting of $CH_2$, $CH_2CH_2$, $CH_2O$, $CH_2S$ and $CH_2SO$; $R_2$ represents a hydrogen atom, a lower alkyl group having 1 to 4 carbon atoms or a benzyl group; $R_3$ represents a group of the general formula $COOR_4$ (wherein $R_4$ represents a hydrogen atom or a lower alkyl group having 1 to 4 carbon atoms), a group of the general formula $NHCOR_5$ (wherein $R_5$ represents an optionally substituted phenyl group), a group of the general formula $CONR_6R_7$ (wherein $R_6$ represents a hydrogen atom or a lower alkyl group having 1 to 4 carbon atoms; and $R_7$ represents a lower alkyl group having 1 to 4 carbon atoms, an optionally substituted phenyl group, a carboxyalkyl group or a lower alkylsulfonyl group), a $PO_3H_2$ group or an $SO_3H$ group; and n is an integer of from 1 to 4.

3 Claims, 1 Drawing Sheet

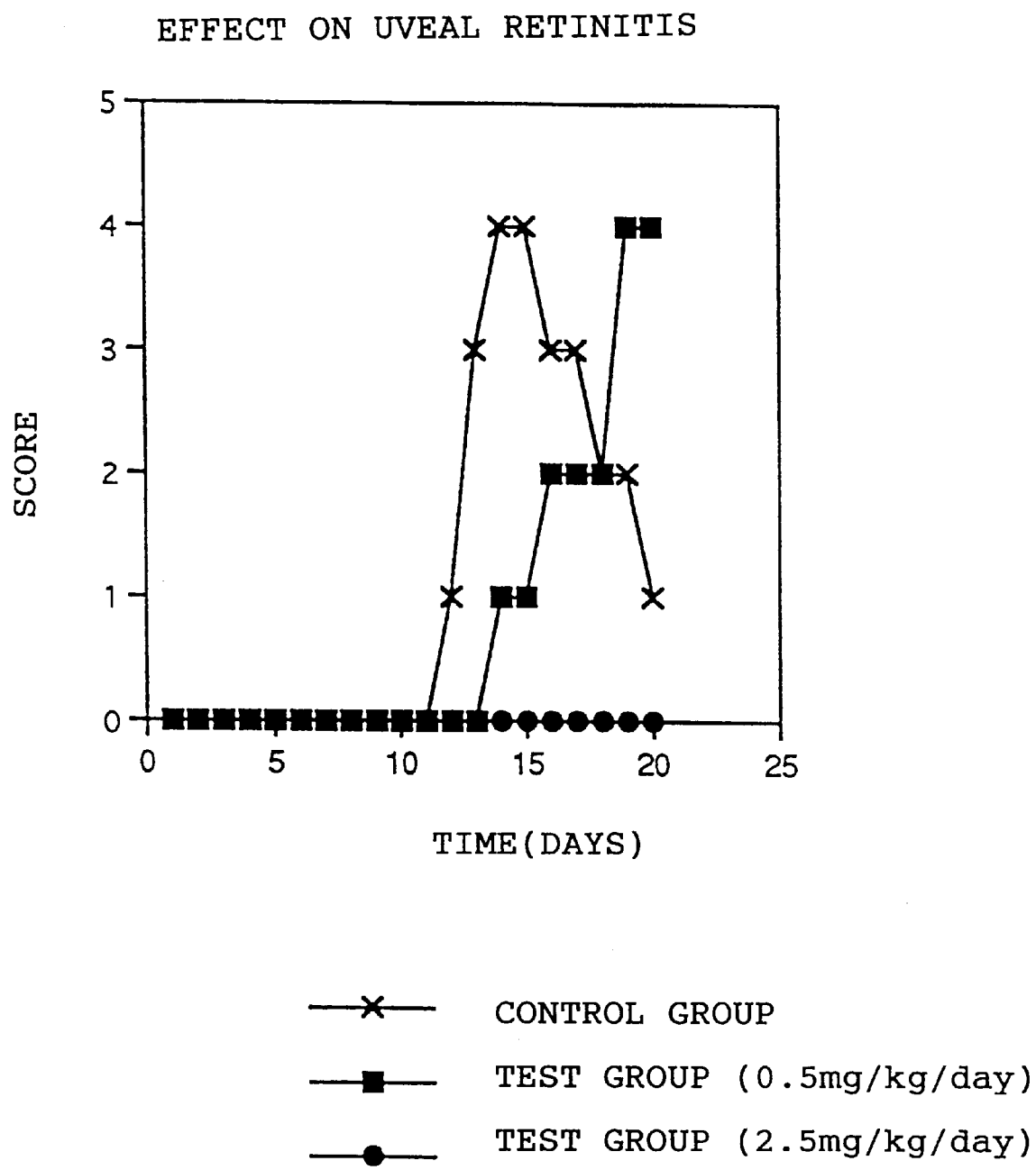

UVEITIS REMEDY

This is a 371 of PCT/JP97/00854 filed Mar. 18, 1997.

TECHNICAL FIELD

This invention relates to drugs containing methotrexate derivatives. More particularly, it relates to drugs containing methotrexate derivatives which are efficacious against uveitis.

BACKGROUND ART

Although uveitis sometimes occurs in association with Behcet's disease, sarcoidosis, Harada's disease, etc., its pathogenesis is obscure in 50 to 70% of the patients. There are a number of findings on uveitis which can be classified into, for example, iridocyclitis (anterior uveitis), retinochoroiditis (posterior uveitis), panuveitis, intermediary uveitis, etc. depending on the inflammation site. To treat uveitis, steroids are commonly used, however, steroids produce undesirable side effects. Therefore, it has been urgently required to develop drugs efficacious against uveitis.

On the other hand, methotrexate (MTX), which is a folic acid metabolism antagonist, has been employed as a carcinostatic agent in treating acute leukemia, malignant lymphoma, etc. Also, MTX is known as an immunosuppressive agent and used mainly for preventing acute graft-versus-host reactions in bone marrow transplantation. Moreover, it is known that administration of MTX in a small dose is efficacious in treating rheumatoid arthritis.

DISCLOSURE OF THE INVENTION

It is an object of the present invention to provide excellent remedies for uveitis.

The present inventors have conducted extensive studies and consequently found that compounds represented by the following general formula (I) or salts thereof are useful as remedies for uveitis, thus completing the present invention:

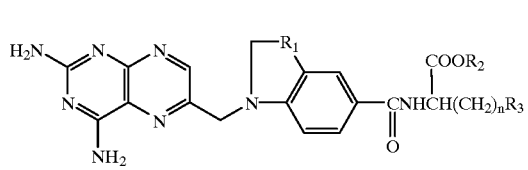

(I)

wherein $R_1$ represents a member selected from the group consisting of $CH_2$, $CH_2CH_2$, $CH_2O$, $CH_2S$ and $CH_2SO$; $R_2$ represents a hydrogen atom, a lower alkyl group having 1 to 4 carbon atoms or a benzyl group; $R_3$ represents a group of the general formula $COOR_4$ (wherein $R_4$ represents a hydrogen atom or a lower alkyl group having 1 to 4 carbon atoms), a group of the general formula $NHCOR_5$ (wherein $R_4$ represents an optionally substituted phenyl group), a group of the general formula $CONR_6R_7$ (wherein $R_6$ represents a hydrogen atom or a lower alkyl group having 1 to 4 carbon atoms; and $R_7$ represents a lower alkyl group having 1 to 4 carbon atoms, an optionally substituted phenyl group, a carboxyalkyl group or a lower alkylsulfonyl group), a $PO_3H_2$ group or an $SO_3H$ group; and n is an integer of from 1 to 4.

Accordingly, the present invention relates to remedies for uveitis which contain, as the active ingredient, one or more compounds represented by the following general formula (I) or salts thereof:

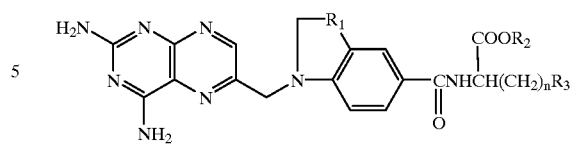

(I)

wherein $R_1$ represents a member selected from the group consisting of $CH_2$, $CH_2CH_2$, $CH_2O$, $CH_2S$ and $CH_2SO$; $R_2$ represents a hydrogen atom, a lower alkyl group having 1 to 4 carbon atoms or a benzyl group; $R_3$ represents a group of the general formula $COOR_4$ (wherein $R_4$ represents a hydrogen atom or a lower alkyl group having 1 to 4 carbon atoms), a group of the general formula $NHCOR_5$ (wherein $R_4$ represents an optionally substituted phenyl group), a group of the general formula $CONR_6R_7$ (wherein $R_6$ represents a hydrogen atom or a lower alkyl group having 1 to 4 carbon atoms; and $R_7$ represents a lower alkyl group having 1 to 4 carbon atoms, an optionally substituted phenyl group, a carboxyalkyl group or a lower alkylsulfonyl group), a $PO_3H_2$ group or an $SO_3H$ group; and n is an integer of from 1 to 4.

The present invention further relates to remedies for uveitis which contain, as the active ingredient, one or more compounds represented by the following general formula (II) or salts thereof:

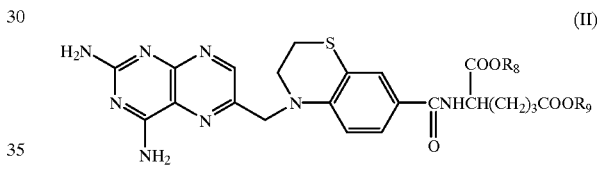

(II)

wherein $R_8$ and $R_9$ are the same or different and each represents a hydrogen atom or a lower alkyl group having 1 to 4 carbon atoms.

BRIEF DESCRIPTION OF THE DRAWING

FIG. 1 is a graph which illustrates the effect of the drugs of the present invention on uveal retinitis.

BEST MODE FOR CARRYING OUT THE INVENTION

The compounds of the present invention represented by the general formula (I) are described in International Publication Gazette WO 92/03436 which provides data showing that these compounds inhibit the proliferation of human lymphocytes, rat and human keratinocytes and mouse cancer cells (P388, colon26). Based on these experimental data, it is suggested in this gazette that these compounds might be useful as remedies for rheumatoid arthritis, psoriasis and cancer. Moreover, International Publication Gazette WO 94/14810 presents data showing that the compounds represented by the general formula (II) inhibit the proliferation of synovial cells from rheumatoid arthritis patients, which suggests that these compounds are useful as antirheumatic agents.

However, it has never been reported so far that the compounds represented by the general formula (I) are efficacious against uveitis.

The drugs of the present invention are useful in treating uveitis. The term "uveitis" as used herein involves uveal retinitis, iridocyclitis (anterior uveitis), retinochoroiditis (posterior uveitis), panuveitis, intermediary uveitis, etc. Uveitis is roughly classified into endogenous uveitis and exogenous uveitis. Although the term "uveitis" as used herein involves both of the endogenous and exogenous ones, the drugs of the present invention are efficacious in particular for endogenous uveitis. Examples of the endogenous uveitis include those induced by Behcet's disease, sarcoidosis and Harada's disease, sympathetic ophthalmitis, etc.

The term "lower alkyl group" as used herein means linear or branched alkyl groups having 1 to 6 carbon atoms, unless the number of carbon atoms is otherwise specified. Preferable examples thereof include methyl, ethyl, n-propyl, isopropyl, n-butyl, isobutyl, sec-butyl, tert-butyl, n-pentyl and n-hexyl groups. Examples of the lower alkyl group having 1 to 4 carbon atoms include methyl, ethyl, n-propyl, isopropyl, n-butyl, isobutyl, sec-butyl and tert-butyl groups.

Examples of the substituent in the optionally substituted phenyl group include lower alkyl, hydroxyl, amino, halogeno, cyano, lower alkyloxy, mercapto, acyl, acyloxy, phenyl, carboxyl and lower alkyloxycarbonyl groups. Among these substituents, carboxyl and lower alkyloxycarbonyl groups are preferable therefor.

The term "carboxyalkyl" group means lower alkyl groups substituted by one or more carboxyl groups. Preferable examples thereof are lower alkyl groups substituted by one carboxyl group. As a particularly preferable example thereof, a 3-carboxypropyl group may be cited.

As a preferable examples of the lower alkylsulfonyl group, a methanesulfonyl group may be cited.

The compounds of the present invention may be used in the form of their salts which are prepared by conventional methods. Examples of the salts usable in the present invention include inorganic acid salts such as hydrochloride, hydrobromide, hyrdoiodide, sulfate and phosphate; organic acid salts such as succinate, malonate, acetate, maleate, fumarate, citrate, gluconate, mandelate, benzoate, salicylate, methanesulfonate, benzenesulfonate and p-toluenesulfonate; and metal salts such as sodium, potassium and magnesium salts. It is preferable to use inorganic acid salts or organic acid salts, still preferably hydrobromide or methanesulfonate, therefor.

Preferable examples of the compounds to be used in the remedies of the present invention include those described in International Publication Gazettes WO 92/03436 and WO 94/14810. Among all, the compound described in Example in International Publication Gazette WO 94/14810 may be cited as the most desirable one.

Although drugs containing the compounds of the present invention may be administered either orally or parenterally, oral administration is particularly preferred. The administration dose usually ranges from 0.01 to 100 mg/day/patient, though it may vary depending on, for example, the disease type and the body weight and conditions of the patient.

Examples of the dosage form of the drugs containing the compounds of the present invention are liquid preparations such as injections, tablets, capsules, dusts, etc.

Also, the drugs of the present invention can be locally administered as, for example, eye drops or injections. The local injection methods are exemplified by intraocular injection, subconjunctival injection and injection under Tenon's capsule.

EXAMPLES

To further illustrate the present invention in greater detail, the following examples will be given wherein N-(1-((2,4-diamino-6-pteridinyl)methyl)-3,4-dihydro-2H-1,4-benzothiazine-7-carbonyl)-L-α-aminoadipic acid of the following formula was employed as the compound of the present invention.

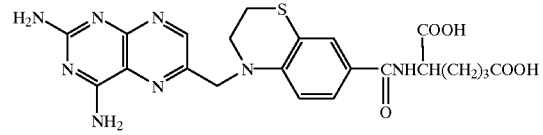

Example 1

Effect on rat experimental autoimmune uveal retinitis

Experimental autoimmune uveal retinitis was induced by immunizing Lewis rats with S antigen together with Freund's complete adjuvant. That is to say, S antigen (50 μg), which had been isolated from bovine retina in accordance with the method of Kozak et al. (Curr. Eye Res., Vol. 1, 327–337, 1981), was dissolved in PBS. Next, the obtained solution was mixed with the same amount of Freund's complete adjuvant (CFA) prepared by suspending Mycobacterium Tuberculosis H37Ra (10 mg/ml) in Freund's incomplete adjuvant (Difco) to give an emulsion. Female Lewis rats aged 8 weeks (Charles River) were immunized by subcutaneously injecting 0.1 ml/animal of this emulsion into the footpad. The severity of uveal retinitis was evaluated by observing the occurrence of intraocular inflammation with the naked eye and scored in 5 grades (0 to 4) as follows.

Score 0: normal.

1: anterior uveitis, with all deposits in the pupil.

2: total invasion of the pupil by the cellular infiltrate.

3: severe inflammation associated with a corneal oedema.

4: ocular proptosis, and haemorrhages in the anterior chamber.

The test compound was dissolved in PBS and then orally administered from the day of the immunization with S antigen (referred to as the day 0) 5 days per week for 3 weeks. The test compound was administered in a dose of 0.5 mg/kg/day or 2.5 mg/kg/day. On the other hand, PBS alone was administered to a control group. Each group had 3 animals and the average score of each group was determined. FIG. 1 shows the results. In the control group, uveal retinitis broke out on the day 12 and the score reached to the maximum level (4) on the day 14. In the group with the administration of 0.5 mg/kg/day of the test compound, the onset of uveal retinitis was delayed. Namely, uveal retinitis broke out on the day 14 and the score reached to 4 on the day 19. In the group with the administration of 2.5 mg/kg/day of the test compound, the onset of uveal retinitis was completely inhibited. These facts indicate that the drugs of the present invention are useful as remedies for uveitis.

Industrial Applicability

As shown in the above examples, it has been confirmed that the drugs of the present invention are efficacious against experimental autoimmune uveal retinitis in rats. This fact suggests that the drugs of the present invention are useful as remedies for uveitis.

What is claimed is:

1. A method for the treatment of a patient suffering from uveitis comprising administering to said patient an amount sufficient for the treatment of said uveitis of one or more compounds of formula (I) or a salt thereof:

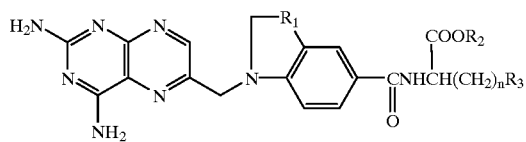

wherein $R_1$ represents a member selected from the group consisting of $CH_2$, $CH_2CH_2$, $CH_2O$, $CH_2S$, and $CH_2SO$; $R_2$ represents a hydrogen atom, a lower alkyl group having 1 to 4 carbon atoms or a benzyl group; $R_3$ represents a group of the general formula $COOR_4$ (wherein $R_4$ represents a hydrogen atom or a lower alkyl group having 1 to 4 carbon atoms), a group of the general formula $NHCOR_5$ (wherein $R_5$ represents an optionally substituted phenyl group), a group of the general formula $CONR_6R_7$ (wherein $R_6$ represents a hydrogen atom or a lower alkyl group having 1 to 4 carbon atoms; and $R_7$ represents a lower alkyl group having 1 to 4 carbon atoms, an optionally substituted phenyl group, a carboxyalkyl group or a lower alkyl-sulfonyl group), a $PO_3H_2$ group or an $SO_3H$ group; and n is an integer of from 1 to 4.

2. The method according to claim 1 wherein said amount sufficient is from 0.01 to 100 mg/day.

3. The method according to claim 1 wherein said one more compounds are in accordance with formula (II):

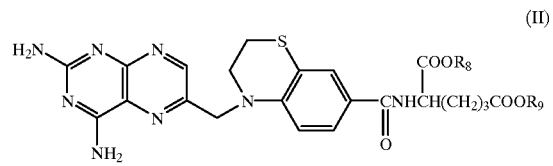

wherein $R_8$ and $R_9$ are the same or different and each represents a hydrogen atom or an alkyl group having 1 to 4 carbon atoms.

* * * * *